US012761212B2

(12) United States Patent
Zhu et al.

(10) Patent No.: US 12,761,212 B2
(45) Date of Patent: Oct. 13, 2026

(54) MICROFLUIDIC CHIP FOR IN-SITU EIS DETECTION OF *CAENORHABDITIS ELEGANS*

(71) Applicant: SOUTHEAST UNIVERSITY, Wuxi (CN)

(72) Inventors: Zhen Zhu, Wuxi (CN); Tiancong Lan, Wuxi (CN); Song Yu, Wuxi (CN)

(73) Assignee: SOUTHEAST UNIVERSITY, Wuxi (CN)

( * ) Notice: Subject to any disclaimer, the term of this patent is extended or adjusted under 35 U.S.C. 154(b) by 133 days.

(21) Appl. No.: 18/857,193

(22) PCT Filed: Feb. 6, 2024

(86) PCT No.: PCT/CN2024/076235

§ 371 (c)(1),
(2) Date: Oct. 16, 2024

(87) PCT Pub. No.: WO2024/188000

PCT Pub. Date: Sep. 19, 2024

(65) Prior Publication Data

US 2025/0271420 A1 Aug. 28, 2025

(30) Foreign Application Priority Data

Mar. 16, 2023 (CN) ......................... 202310255378.5

(51) Int. Cl.
*G01N 33/50* (2006.01)

(52) U.S. Cl.
CPC .................... *G01N 33/5085* (2013.01); *G01N 2333/43534* (2013.01)

(58) Field of Classification Search
CPC ..... G01N 33/5085; G01N 2333/43534; G01N 27/02; B01L 2300/0645; B01L 3/502707;
(Continued)

(56) References Cited

U.S. PATENT DOCUMENTS

2009/0317798 A1* 12/2009 Heid ..................... B01L 3/5027 435/6.12
2010/0024572 A1* 2/2010 Roukes .............. G01N 33/5032 216/17
(Continued)

FOREIGN PATENT DOCUMENTS

CN 107942083 A 4/2018
CN 111735852 A 10/2020
(Continued)

OTHER PUBLICATIONS

Zhu et al., Using microfluidic impedance cytometry to measure C. elegans worms and identify their developmental stages, Sensors and actuators B: Chemical, 2018, 275, 470-482 (Year: 2018).*
(Continued)

*Primary Examiner* — Shizhi Qian
(74) *Attorney, Agent, or Firm* — Bayramoglu Law Offices LLC

(57) ABSTRACT

A microfluidic chip for in-situ EIS detection of *C. elegans* is provided. The chip has three layers of structures. A lower layer is a glass substrate integrated with a micro-electrode array and is used for EIS measurement and *C. elegans* deflection. A middle layer is a fluidic channel layer and is formed by a *C. elegans* perfusion channel, a storage chamber, a deflection channel, an EIS measurement chamber and a fluidic outlet channel connected in sequence. An upper layer is a pneumatic valve channel layer, and storage chamber control valves of the pneumatic valve channel layer are used for controlling *C. elegans* to enter or come out of the storage chamber. A deflection channel control valve is used for controlling *C. elegans* to enter the measurement chamber. A *C. elegans* capture valve is used for controlling *C. elegans* in the EIS measurement chamber to be captured and released.

8 Claims, 3 Drawing Sheets

(58) Field of Classification Search
CPC ... B01L 3/502715; B01L 3/5027; Y02A 50/30
See application file for complete search history.

(56) References Cited

U.S. PATENT DOCUMENTS

| | | | | |
|---|---|---|---|---|
| 2010/0263599 | A1* | 10/2010 | Yanik | G01N 33/5082 604/93.01 |
| 2012/0061240 | A1 | 3/2012 | Selvaganapathy et al. | |
| 2016/0236195 | A1* | 8/2016 | Daridon | C12M 1/34 |
| 2017/0312748 | A1* | 11/2017 | Cornaglia | B01L 3/5085 |
| 2020/0363401 | A1* | 11/2020 | Ricicova | G01N 33/5052 |
| 2021/0394180 | A1 | 12/2021 | Sarioglu et al. | |
| 2022/0146498 | A1* | 5/2022 | Vanapalli | G01N 33/5085 |
| 2022/0169965 | A1* | 6/2022 | Kamm | B01L 3/502761 |

FOREIGN PATENT DOCUMENTS

| | | | |
|---|---|---|---|
| CN | 114289082 | A | 4/2022 |
| CN | 114289084 | A | 4/2022 |
| CN | 116237099 | A | 6/2023 |
| KR | 20120086188 | A | 8/2012 |

OTHER PUBLICATIONS

Yang et al., A microfluidic diode for sorting and immobilization of Caenorhabditis elegans, Biomedical microdevices, 2017, 19, 38 (Year: 2017).*

Chaudhury, Bio-micro-systems for diagnostic applications, disease prevention and creating tools for biological research, PhD thesis of the University of Michigan, 2018 (Year: 2018).*

Midkiff et al., Microfluidic Technologies for High Throughput Screening Through Sorting and On-Chip Culture of C. elegans, Molecules, 2019, 24, 4292 (Year: 2019).*

Honrado et al., Single cell microfluidic impedance cytometry: from raw signals to cell phenotypes using data analytics, Lab on a chip, 2021, 21, 22-54 (Year: 2021).*

Zhang et al., Advances in C. elegans behavior research with microfluidic devices and its future prospects in the evaluation of exogenous pollutants, TrAC trends in analytical chemistry, 2021, 136, 116195 (Year: 2021).*

Christopher B. Rohde, et al, Microfluidic system for on-chip high-throughput whole-animal sorting and screening at subcellular resolution, Proceedings of the National Academy of Sciences of the United States of America, 2007, pp. 13891-13895, vol. 104 No. 35.

* cited by examiner

MICROFLUIDIC CHIP FOR IN-SITU EIS DETECTION OF *CAENORHABDITIS ELEGANS*

CROSS REFERENCE TO THE RELATED APPLICATIONS

This application is the national phase entry of International Application No. PCT/CN2024/076235, filed on Feb. 6, 2024, which is based upon and claims priority to Chinese Patent Application No. 202310255378.5, filed on Mar. 16, 2023, the entire contents of which are incorporated herein by reference.

TECHNICAL FIELD

The invention belongs to the field of microfluidic chips and micro-nano machining, and particularly relates to a microfluidic chip for in-situ EIS detection of *Caenorhabditis elegans* (*C. elegans*).

BACKGROUND

Microfluidics is a technology for accurately manipulating microfluidics; it explores spatial features on a scale typically ranging from 1 μm to 1 mm. The basic microfluidic technology is featured with small capacity, small size, low energy consumption and high device integration, and the like. This technology is generally implemented by specific microfluidic chips fabricated by micro-nano machining and is a multi-cross field including engineering science, hydromechanics, electromagnetics, optics, chemistry, micromachining, bioengineering and other disciplines. At present, microfluidic chips integrated with a micro-electrode array become effective means for researching microbiological-electronics, have been applied to multiple fields such as DNA molecular detection, unicellular detection, microspheroid detection and model organism detection, witness a rapid development, and have a great research potential.

*C. elegans*, as a common model organism, is widely applied to cell apoptosis, senescence, nervous systems, meiosis and other research fields. Researches that directly use *C. elegans* have won the Nobel prize three times, indicating that *C. elegans* has great research value. Compared with other model organisms, *C. elegans* becomes an ideal model in organism senescence, sexual propagation and other fields because it has the following features:

(1) *C. elegans* has a small size and a high fecundity and can be bred in mass at room temperature;

(2) *C. elegans* has a short life and can grow into adults in 3-4 days, and the average life of *C. elegans* is about 2-3 weeks;

(3) *C. elegans* is transparent, allowing structures and fluorescent modifications in *C. elegans* to be microscopically observed easily;

(3) Upon whole genome sequencing, gene analysis and gene modification can be carried out on *C. elegans* easily, and about 40% of the genes of *C. elegans* are homologous to the genes of humans.

(5) *C. elegans* has sex chromosomes and can be used for genetic research, sexual propagation such as meiosis, and other researches.

Electrical impedance spectroscopy (EIS), as non-intrusive, label-free and multi-parameter detection technique, can accurately and quantitatively analyze the complex impedance of a system to be detected by applying sweep-frequency alternating-current stimuli on the system and detecting response signals. At present, EIS is widely applied to electrochemical analysis, food safety inspection, environmental monitoring, corrosion mechanism research, biomedical research and many other fields. In the field of biomedical research, EIS is applied to multiple levels such as biomacromolecules, cells, tissues, and model organisms.

At present, although in-situ EIS detection based on microfluidics has been widely applied to cell research, EIS detection for *C. elegans* research still remains at the elementary stage and mainly has the following problems: first, the motion of *C. elegans* has a great influence on impedance measurement, and the *C. elegans* is difficult to immobilize, making it impossible to guarantee the measurement accuracy; in addition, the *C. elegans* is long and thin in bodily form, making it impossible to measure the impedance of all portions of the *C. elegans* by means of a single pair of electrodes; moreover, the flux of in-situ EIS detection is low, making it impossible to guarantee the measurement efficiency. Therefore, in order to realize high-efficiency, high-accuracy and multi-site in-situ EIS detection of *C. elegans*, it is necessary to develop a microfluidic chip for in-situ EIS detection of *C. elegans*, which is integrated with a micro-electrode array, a measurement line and a *C. elegans* immobilizing valve.

SUMMARY

The objective of the invention is to provide a microfluidic chip for in-situ EIS detection of *C. elegans* to solve the technical problems that the motion of *C. elegans* has a great influence on impedance measurement and the *C. elegans* is difficult to immobilize, making it impossible to guarantee the measurement accuracy, that the *C. elegans* is long and thin in bodily form, making it impossible to measure the impedance of all portions of the *C. elegans* by means of a single pair of electrodes, and that the flux of in-situ EIS detection is low, making it impossible to guarantee the measurement efficiency.

To solve the above technical problems, the specific technical solution of the invention is as follows:

A microfluidic chip for in-situ EIS detection of *C. elegans* includes a glass substrate layer, a fluidic channel layer and a pneumatic valve channel layer, wherein the glass substrate layer, the fluidic channel layer and the pneumatic valve channel layer are connected by means of screws;

the glass substrate layer, as a base of the whole chip, is used for supporting upper structures, and a micro-electrode array is integrated on the glass substrate layer;

the fluidic channel layer includes a *C. elegans* perfusion channel, a storage chamber, a deflection channel, an EIS measurement chamber and a fluidic outlet channel; wherein, the *C. elegans* perfusion channel, the storage chamber, the deflection channel, the EIS measurement chamber and the fluidic outlet channel are connected in sequence; a measurement medium injection channel is connected between the deflection channel and the EIS measurement chamber;

the storage chamber is used for storing *C. elegans* samples to be measured;

the deflection channel allows *C. elegans* to deflect therein freely;

the EIS measurement chamber is in indirect contact with electrodes below;

the pneumatic valve channel layer includes storage chamber control valves, a deflection channel control valve, a *C. elegans* capture valve and a *C. elegans* immobilizing valve, wherein:

two storage chamber control valves are respectively located above slits in two sides of the storage chamber and used for controlling *C. elegans* to enter or come out of the storage chamber;

the deflection channel control valve is located above slits between the deflection channel and the EIS measurement chamber and used for controlling *C. elegans* to enter the EIS measurement chamber;

the *C. elegans* capture valve is located above slits between the EIS measurement chamber and the fluidic outlet channel and used for controlling *C. elegans* in the EIS measurement chamber to be captured and released;

the *C. elegans* immobilizing valve is located above the whole EIS measurement chamber, a pneumatic valve channel has a width greater than a width of the EIS measurement chamber, and the *C. elegans* immobilizing valve is used for immobilizing *C. elegans* entering a measurement channel;

the micro-electrode array includes square electrode pins located around the chip and connected to a measurement circuit, and functional structures located around the EIS measurement chamber and the deflection channel;

the functional structures are divided into two groups, a first group includes deflection electrode pairs located on two sides of the deflection channel and used for controlling *C. elegans* to deflect, and a second group includes EIS measurement electrodes located around the EIS measurement chamber and used for measuring EIS signals of *C. elegans* at different positions;

the storage chamber and the storage chamber control valves on the two sides of the storage chamber form a *C. elegans* storage region; one-time injection and storage of *C. elegans* is completed in the *C. elegans* storage region; when the control valve on an inlet side of the storage chamber is opened and the control valve on an outlet side of the storage chamber is closed, the *C. elegans* is injected; when the control valve on the inlet side of the storage chamber is closed and the control valve on the outlet side of the storage chamber is opened, the *C. elegans* enters the deflection channel;

the EIS measurement chamber, the measurement medium injection channel, the EIS measurement electrodes, the *C. elegans* capture valve and the *C. elegans* immobilizing valve form an EIS measurement region; in-situ EIS measurement of *C. elegans* on multiple sites is implemented in the EIS measurement region;

the deflection channel, the deflection electrode pairs and the deflection channel control valve forms a *C. elegans* deflection region; quick deflection of *C. elegans* that is about to enter the EIS measurement region is implemented in the *C. elegans* deflection region;

the *C. elegans* storage region, the *C. elegans* deflection region and the EIS measurement region form a measurement line.

Further, the pneumatic valve channel layer is prepared from PDMS by soft lithography.

Further, the micro-electrode array is made from chromium-copper (Cr—Au) or tungsten titanium-platinum (TiW—Pt).

Further, the storage chamber is circular; the deflection channel is configured as a strip-shaped structure and has a width that is twice a width of adult *C. elegans*; the EIS measurement chamber is configured as a strip-shaped structure and has a width that is greater than the width of the adult *C. elegans*, and multiple pairs of slits are uniformly distributed in two sides of the EIS measurement chamber.

Further, joints between the *C. elegans* perfusion channel, the storage chamber, the deflection channel and the EIS measurement chamber are all shaped like an inverted triangle and work together with control valves to open or close the corresponding channels; inverted triangle-shaped slits allow *C. elegans* to pass through one by one.

Further, the glass substrate layer, the fluidic channel layer and the pneumatic valve channel layer are fixedly connected by multi-layer bonding, wherein the glass substrate layer is located at the bottom, the fluidic channel layer is located in the middle, and the pneumatic valve channel layer is located at the top.

Further, the glass substrate layer integrated with the micro-electrode array is isolated from the fluidic channel layer by means of a silicon nitride passivation layer, and the fluidic channel layer is isolated from the pneumatic valve channel layer by means of a PDMS film.

Further, lateral electrodes in the EIS measurement electrodes of the micro-electrode array are liquid electrodes, that is, the lateral electrodes are in indirect contact with the measurement chamber by means of slits of a fluidic channel rather than being in direct contact with measurement chamber.

The microfluidic chip for in-situ EIS detection of *C. elegans* provided by the invention has the following advantages: the chip is designed and machined by means of the micro-nano machining technique, and the microfluidic technology and the EIS technology are combined; the chip adopts a multi-layer design in structure and introduces the concept of assembly line; and high-efficiency, high-accuracy and multi-site in-situ EIS detection of *C. elegans* is realized.

Reference signs: 1, glass substrate; 2, *C. elegans* perfusion channel; 3, *C. elegans* storage region; 4, storage chamber; 5, *C. elegans* deflection region; 6, deflection channel; 7, measurement medium injection channel; 8, deflection electrode pair; 9, EIS measurement chamber; 10, EIS measurement region; 11, fluidic outlet channel; 12, EIS measurement electrode; 13, *C. elegans* capture valve; 14, *C. elegans* immobilizing valve; 15, deflection channel control valve; 16, storage chamber control valve; 601, pneumatic valve channel layer; 602, fluidic channel layer.

DETAILED DESCRIPTION OF THE EMBODIMENTS

To gain a better understanding of the purposes, structures and functions of the invention, a microfluidic chip for in-situ EIS detection of *C. elegans* provided by the invention is described in further detail below in conjunction with accompanying drawings.

Figure 1:
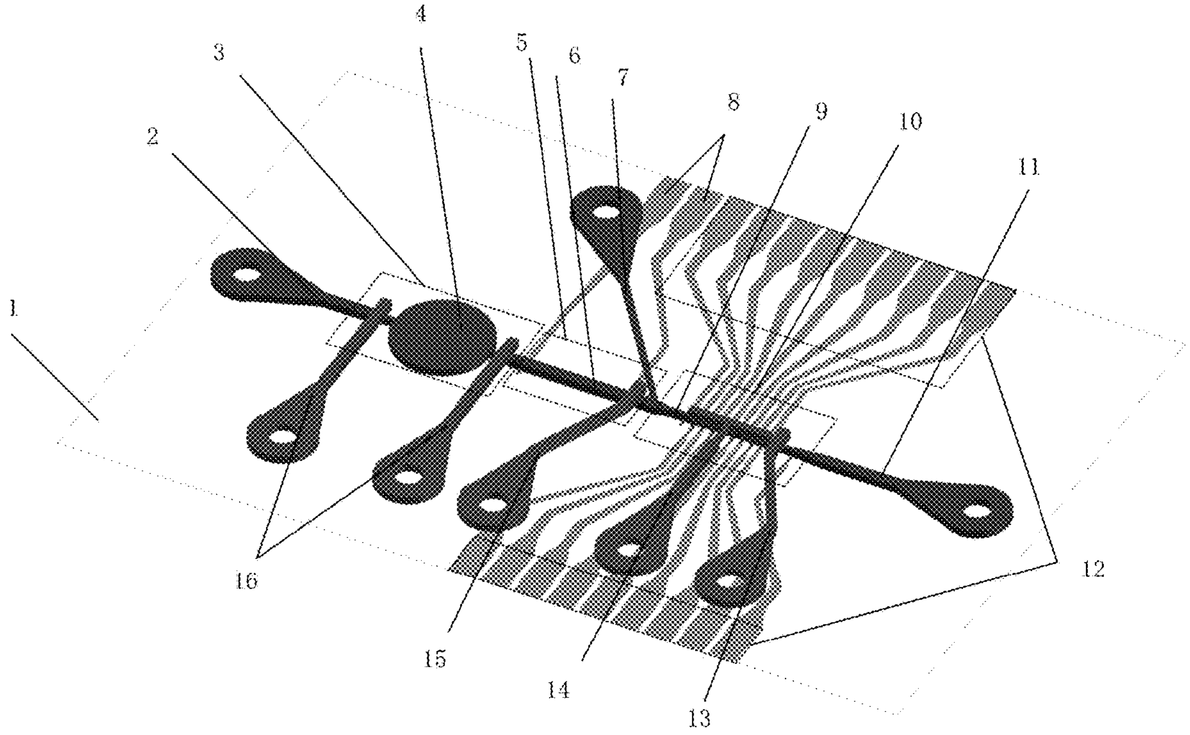
FIG. 1 is a schematic structural view of a microfluidic chip for in-situ EIS detection of *C. elegans* according to the invention.
Figure 2:
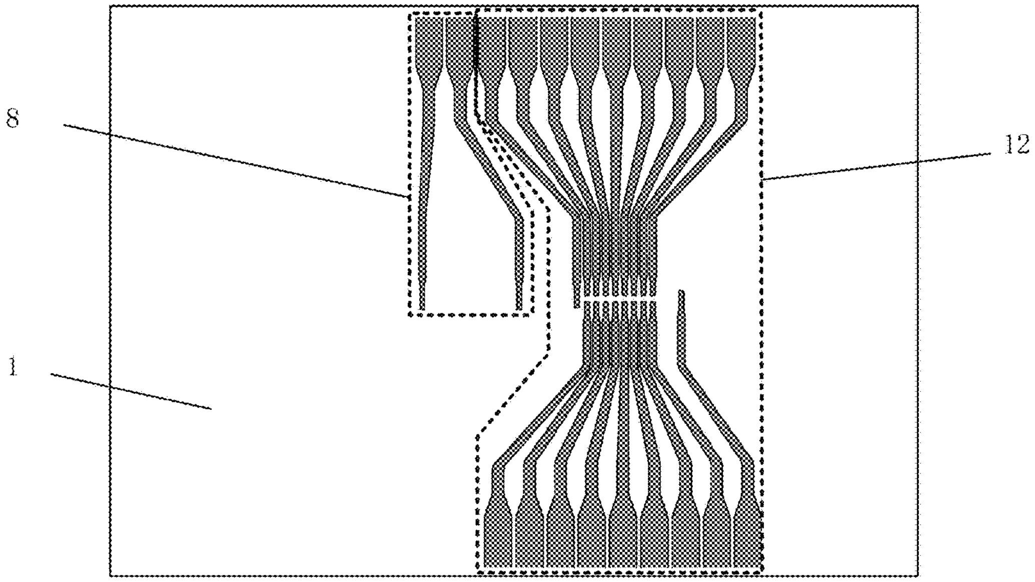
FIG. 2 is a two-dimensional structural view of a glass substrate and electrodes according to the invention.
Figure 3:
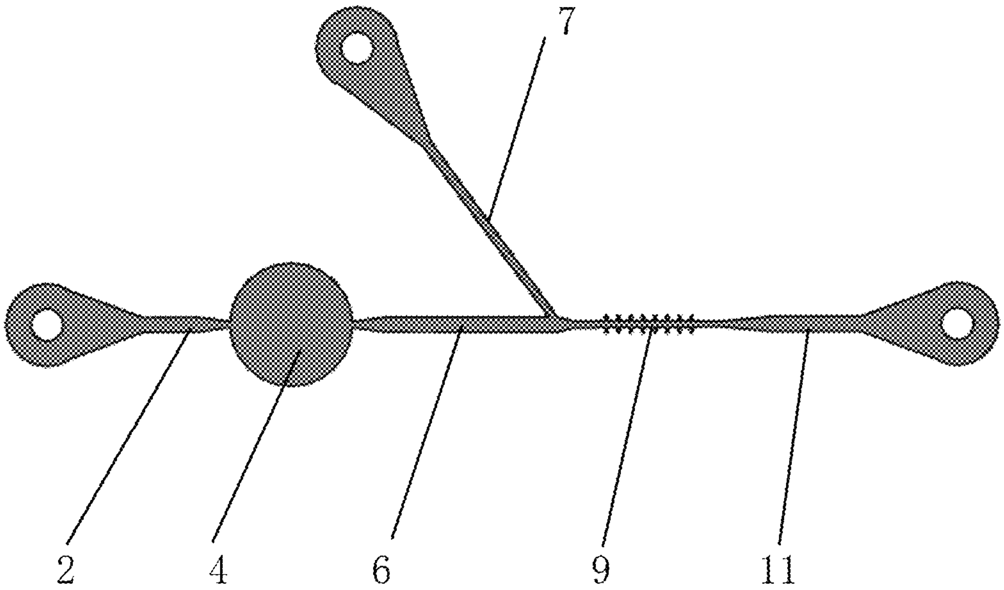
FIG. 3 is a two-dimensional structural view of a fluidic channel according to the invention.
Figure 4:
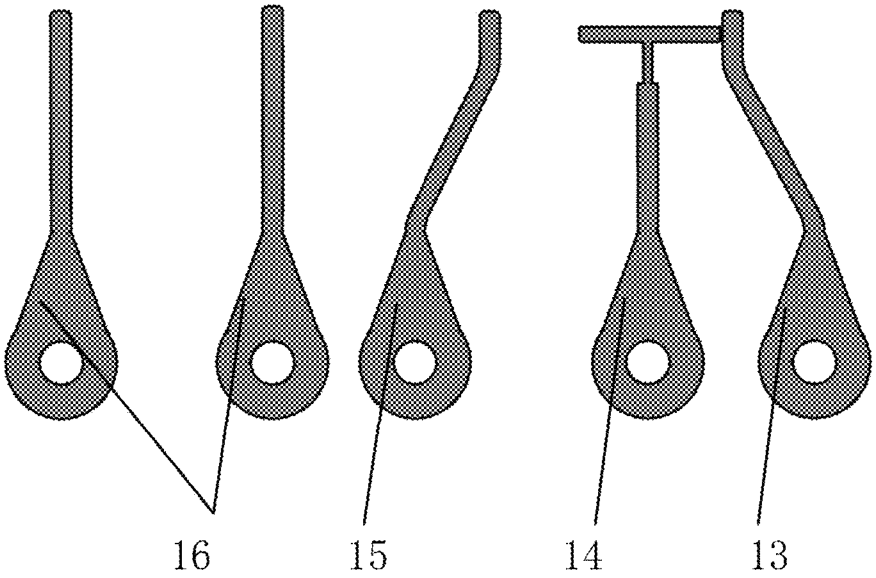
FIG. 4 is a two-dimensional structural view of a pneumatic membrane valve channel according to the invention; 5
Figure 5:
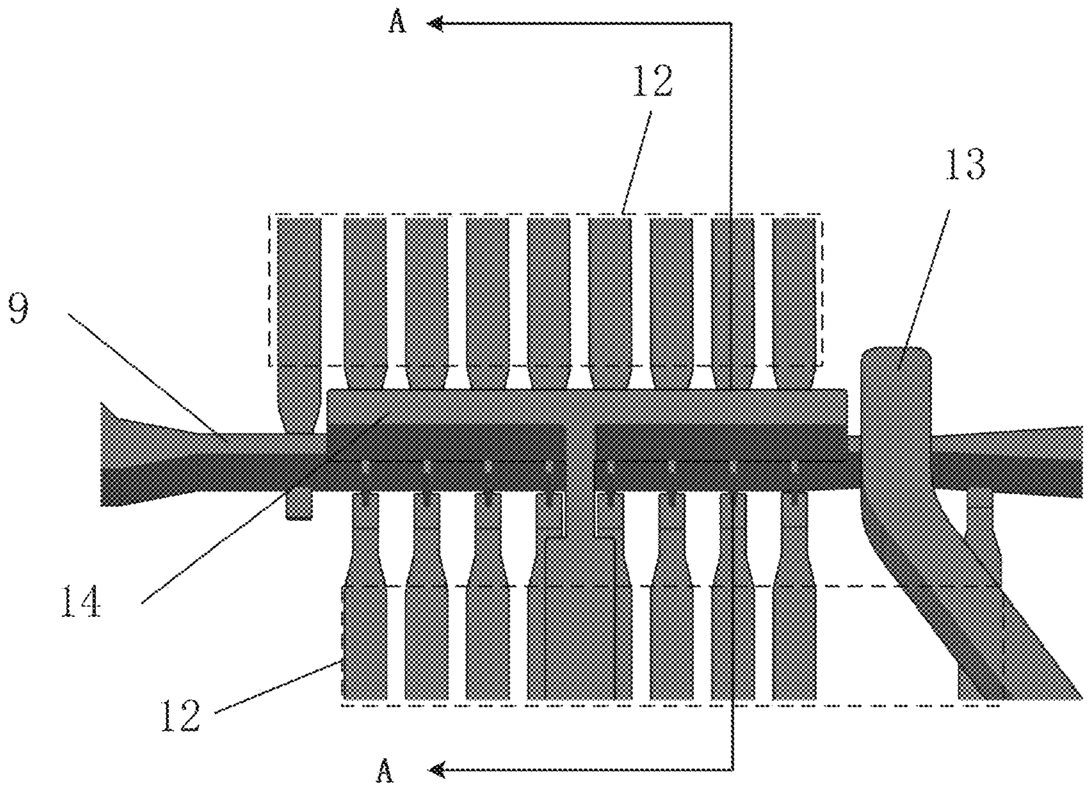
FIG. 5 is a three-dimensional structural view of an electric impedance measurement region according to the invention.
Figure 6:
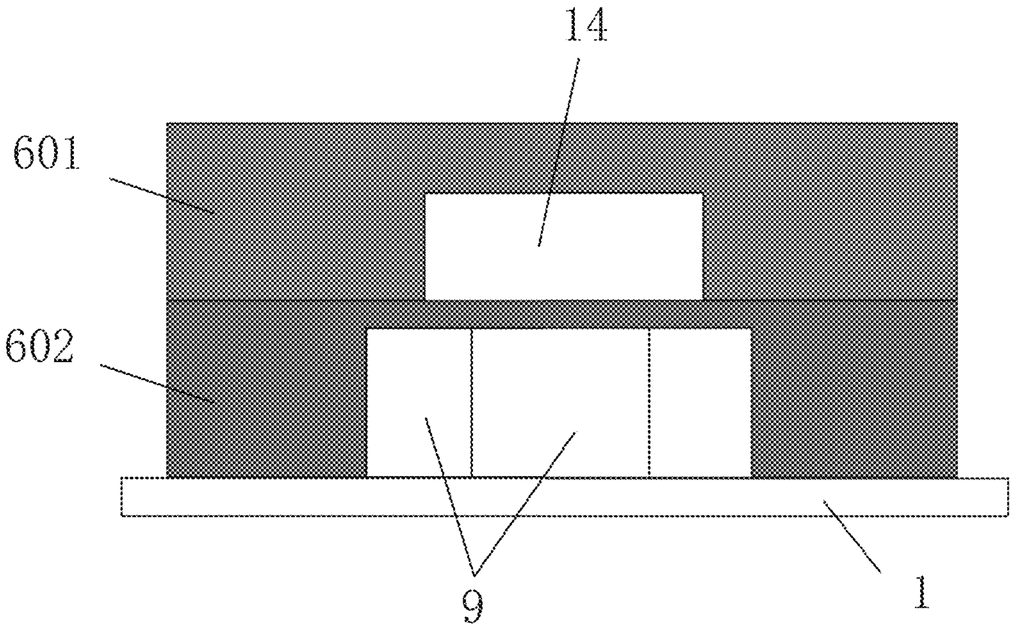
FIG. 6 is a sectional structural view along A-A of a three-dimensional structure of the electric impedance measurement region according to the invention.

Refer to FIG. 1 which is a schematic structural view of the microfluidic chip for in-situ EIS detection of *C. elegans* according to one embodiment of the invention.

The microfluidic chip for in-situ EIS detection of *C. elegans* structurally includes a glass substrate layer 1, a fluidic channel layer 602 and a pneumatic valve channel layer 601. Wherein:

the glass substrate layer 1, as a base of the whole chip, is used for supporting upper structures, and a micro-electrode array is integrated on the glass substrate layer 1.

The micro-electrode array includes square electrode pins located around the chip and connected to a measurement circuit, and functional structures located around an EIS measurement chamber 9 and a deflection channel 6;

the functional structures are divided into two groups, wherein a first group includes deflection electrode pairs 8 located on two sides of the deflection channel 9 and used for controlling *C. elegans* to deflect, and a second group includes EIS measurement electrodes 12 located around the EIS measurement chamber 9 and used for measuring EIS signals of the *C. elegans* at different positions;

the micro-electrode array is made from Cr—Au, wherein Cr forms a seed layer and has a thickness of 50 nm, and Au forms an electrode layer and has a thickness of 150 nm;

a silicon nitride film with a thickness of 500 nm is deposited on the micro-electrode array and functions as a passivation layer.

Lateral electrodes in the EIS measurement electrodes 12 of the micro-electrode array are liquid electrodes, that is, the lateral electrodes are in indirect contact with the measurement chamber by means of slits of a fluidic channel rather than being in direct contact with measurement chamber.

The fluidic channel layer 602 includes a *C. elegans* perfusion channel 2, a storage chamber 4, the deflection channel 6, the EIS measurement chamber 9 and a fluidic outlet channel 11 which are connected in sequence. A measurement medium injection channel 7 is connected between the deflection channel 6 and the EIS measurement chamber 9. Wherein:

the storage chamber 4 is circular and used for storing *C. elegans* samples to be measured;

the deflection channel 6 is a configured as a strip-shaped structure and has a width that is about twice the width of adult *C. elegans* to allow the *C. elegans* to deflect freely in the deflection channel 6;

the EIS measurement chamber 9 is configured as a strip-shaped structure, has a width that is slightly greater than the width of adult *C. elegans*, and is in indirect contact with electrodes below by means of eight pairs of slits uniformly distributed in two sides of a channel.

Joints between the *C. elegans* perfusion channel 2, the storage chamber 4, the deflection channel 6 and the EIS measurement chamber 9 are all shaped like an inverted triangle and work together with control valves to open or close the corresponding channels. The inverted triangle-shaped slits allow *C. elegans* to pass through one by one.

The pneumatic valve channel layer 601 includes storage chamber control valves 16, a deflection channel control valve 15, a *C. elegans* capture valve 13 and a *C. elegans* immobilizing valve 14, wherein:

two pairs of storage chamber control valves 16 are respectively located above inverted triangle-shaped slits in two sides of the storage chamber 4 and used for controlling *C. elegans* to enter or come out of the storage chamber.

The deflection channel control valve 15 is located above slits between the deflection channel 6 and the EIS measurement chamber 9 and used for controlling *C. elegans* to enter the EIS measurement chamber 9.

The *C. elegans* capture valve 13 is located above slits between the EIS measurement chamber 9 and the fluidic outlet channel 11 and used for controlling *C. elegans* in the EIS measurement chamber 9 to be captured and released.

The *C. elegans* immobilizing valve 14 is located above the whole EIS measurement chamber 9, a pneumatic valve channel has a width slightly greater than the width of the EIS measurement chamber 9, and the *C. elegans* immobilizing valve 14 is used for immobilizing *C. elegans* entering a measurement channel.

The microfluidic chip for in-situ EIS detection of *C. elegans* is fabricated by a multi-layer bonding process, wherein the glass substrate layer 1 integrated with the micro-electrode array is isolated from the fluidic channel layer 602 by means of the silicon nitride passivation layer, and the fluidic channel layer 602 is isolated from the pneumatic valve channel layer 601 by means of a polydimethylsiloxane (PDMS) film.

The micro-electrode array on the glass substrate layer 1 is obtained by lithography and developing with an AZ5214 photoresist and Au electron beam evaporation. Finally, the passivation layer is obtained by plasma-enhanced chemical vapor deposition and reactive-ion etching.

The fluidic channel layer 602 and the pneumatic valve channel layer 601 are both prepared from PDMS by soft lithography, which specifically includes preparing a silanized mold, mixing the PDMS and a curing agent in proportion, degassing to remove bubbles, pouring the PDMS on the mold, baking the PDMS, stripping the PDMS from the mold, and cutting and perforating the PDMS. Wherein, the mold is an SU-8 male mold.

During PDMS pouring of the fluidic channel layer 602, the thickness is controlled by means of a spinner, and the fluidic channel layer 602 is stripped after the fluidic channel layer 602 and the pneumatic valve channel layer 601 are bonded.

The glass substrate layer 1, the fluidic channel layer 602 and the pneumatic valve channel layer 601 are bonded by means of a bonder according to alignment marks on these layers after plasma activation, and are then heated at 90° C. for 30 min.

The microfluidic chip for in-situ EIS detection of *C. elegans* provided by the invention functionally includes a *C. elegans* storage region 3, a *C. elegans* deflection region 5 and an EIS measurement region 10. The *C. elegans* storage region 3, the *C. elegans* deflection region 5 and the EIS measurement region 10 form a measurement line, which can complete deflection of the next *C. elegans* while the EIS of the previous *C. elegans* is measured, and the next *C. elegans* enters the measurement channel when the previous *C. elegans* is measured and discharged out of the measurement channel. This process is repeated in this way.

The *C. elegans* storage region 3 includes the storage chamber 4 and the storage chamber control valves 16 located on the two sides of the storage chamber 4, and is mainly used for one-time injection and storage of a large batch of *C. elegans*. When the control valve on an inlet side of the storage chamber 4 is opened and the control valve on an outlet side of the storage chamber 4 is closed, *C. elegans* is injected. When the control valve on the inlet side of the storage chamber 4 is closed and the control valve on the outlet side of the storage chamber 4 is opened, the *C. elegans* enters the deflection channel.

The *C. elegans* deflection region 5 includes the deflection channel 6, the deflection electrode pair 8 and the deflection channel control valve 15, and is mainly used for realizing quick deflection of *C. elegans* that is about to enter the EIS measurement region 10. By means of the galvanotaxis of *C. elegans*, that is, *C. elegans* will tend to move towards a low potential, *C. elegans* can be quickly guided to move rightwards by applying an electric field from left to right in the measurement region, and under the action of the deflection channel control valve, it is guaranteed that *C. elegans* enters the EIS measurement region 10 after deflection The EIS measurement region 10 includes the EIS measurement chamber 9, the measurement medium injection channel 7, the EIS measurement electrodes 12, the *C. elegans* capture valve 13 and the *C. elegans* immobilizing valve 14, and is mainly used for implementing in-situ EIS measurement of *C. elegans* on multiple sites. Wherein, the *C. elegans* capture valve 13 and the *C. elegans* immobilizing valve 14 are used together to capture *C. elegans* and keep the *C. elegans* stable in the measurement process, and a measurement medium and other solutions required by experiments are injected by means of the measurement medium injection channel 7. The EIS measurement electrodes 12 cyclically scan EIS signals of the *C. elegans* on different sites. After measurement, the *C. elegans* capture valve and the *C. elegans* immobilizing valve are opened to release the *C. elegans*. The deflection process and the measurement process can be implemented repeatedly to complete quick in-situ EIS measurement of a large batch of *C. elegans.*

It can be understood that although the invention has been described with reference to some embodiments, those skilled in the art can make various modifications or equivalent substitutions to the features and embodiments described above without departing from the spirit and scope of the invention. In addition, under the enlightenment of the invention, these features and embodiments can be modified to adapt to specific conditions and materials without departing from the spirit and scope of the invention. Therefore, the invention is not limited to the specific embodiments disclosed here, and all embodiments falling within the scope of the claims of the application should fall within the protection scope of the invention.

What is claimed is:

1. A microfluidic chip for an in-situ electrical impedance spectroscopy (EIS) detection of *Caenorhabditis elegans* (*C. elegans*), comprising a glass substrate layer, a fluidic channel layer, and a pneumatic valve channel layer, wherein the glass substrate layer, the fluidic channel layer, and the pneumatic valve channel layer are connected by means of screws;

the glass substrate layer, as a base of the microfluidic chip, is configured for supporting upper structures, and a micro-electrode array is integrated on the glass substrate layer;

the fluidic channel layer comprises a *C. elegans* perfusion channel, a storage chamber, a deflection channel, an EIS measurement chamber, and a fluidic outlet channel; wherein the *C. elegans* perfusion channel, the storage chamber, the deflection channel, the EIS measurement chamber, and the fluidic outlet channel are connected in sequence; a measurement medium injection channel is connected between the deflection channel and the EIS measurement chamber;

wherein the storage chamber is configured for storing *C. elegans* samples to be measured;

wherein the deflection channel allows the *C. elegans* to deflect therein freely;

wherein the EIS measurement chamber is in indirect contact with electrodes below;

wherein the pneumatic valve channel layer comprises storage chamber control valves, a deflection channel control valve, a *C. elegans* capture valve, and a *C. elegans* immobilizing valve, wherein two of the storage chamber control valves are respectively located above slits in an inlet side and an outlet side of the storage chamber and configured for controlling the *C. elegans* to enter or come out of the storage chamber;

wherein the deflection channel control valve is located above slits between the deflection channel and the EIS measurement chamber and configured for controlling the *C. elegans* to enter the EIS measurement chamber;

wherein the *C. elegans* capture valve is located above slits between the EIS measurement chamber and the fluidic outlet channel and configured for controlling the *C. elegans* in the EIS measurement chamber to be captured and released;

wherein the *C. elegans* immobilizing valve is located above the EIS measurement chamber, a pneumatic valve channel has a width greater than a width of the EIS measurement chamber, and the *C. elegans* immobilizing valve is configured for immobilizing the *C. elegans* entering a measurement channel;

wherein the micro-electrode array comprises square electrode pins located around the microfluidic chip and connected to a measurement circuit, and functional structures located around the EIS measurement chamber and the deflection channel;

wherein the functional structures are divided into two groups, a first group comprises deflection electrode pairs located on two sides of the deflection channel and configured for controlling the *C. elegans* to deflect, and a second group comprises EIS measurement electrodes located around the EIS measurement chamber and configured for measuring EIS signals of the *C. elegans* at different positions;

wherein the storage chamber and the storage chamber control valves on the inlet side and the outlet side of the storage chamber form a *C. elegans* storage region; a one-time injection and a storage of the *C. elegans* is completed in the *C. elegans* storage region; when the storage chamber control valve on the inlet side of the storage chamber is opened and the storage chamber control valve on the outlet side of the storage chamber is closed, the *C. elegans* is injected; when the storage chamber control valve on the inlet side of the storage chamber is closed and the storage chamber control valve on the outlet side of the storage chamber is opened, the *C. elegans* enters the deflection channel;

wherein the EIS measurement chamber, the measurement medium injection channel, the EIS measurement electrodes, the *C. elegans* capture valve, and the *C. elegans* immobilizing valve form an EIS measurement region-; an in-situ EIS measurement of the *C. elegans* on a plurality of sites is implemented in the EIS measurement region;

wherein the deflection channel, the deflection electrode pairs, and the deflection channel control valve form a

*C. elegans* deflection region; deflection of the *C. elegans* to enter the EIS measurement region is implemented in the *C. elegans* deflection region;

wherein the *C. elegans* storage region, the *C. elegans* deflection region, and the EIS measurement region form a measurement line.

2. The microfluidic chip for the in-situ EIS detection of the *C. elegans* according to claim 1, wherein the pneumatic valve channel layer is prepared from polydimethylsiloxane (PDMS) by soft lithography.

3. The microfluidic chip for the in-situ EIS detection of the *C. elegans* according to claim 1, wherein the micro-electrode array is made from Cr—Au or TiW—Pt.

4. The microfluidic chip for the in-situ EIS detection of the *C. elegans* according to claim 1, wherein the storage chamber is circular; the EIS measurement chamber is configured as a strip-shaped structure and has a width greater than a width of adult *C. elegans*; and a plurality of pairs of slits are uniformly distributed in two sides of the EIS measurement chamber.

5. The microfluidic chip for the in-situ EIS detection of the *C. elegans* according to claim 1, wherein joints between the *C. elegans* perfusion channel, the storage chamber, the deflection channel, the EIS measurement chamber, and the fluidic outlet channel are shaped like an inverted triangle and work together with the deflection channel control valve, the storage chamber control valves, and the *C. elegans* capture valve to open or close the corresponding channels; inverted triangle-shaped slits allow the *C. elegans* to pass through one by one.

6. The microfluidic chip for the in-situ EIS detection of the *C. elegans* according to claim 1, wherein the glass substrate layer, the fluidic channel layer, and the pneumatic valve channel layer are fixedly connected by multi-layer bonding.

7. The microfluidic chip for the in-situ EIS detection of the *C. elegans* according to claim 1, wherein the glass substrate layer integrated with the micro-electrode array is isolated from the fluidic channel layer by means of a silicon nitride passivation layer, and the fluidic channel layer is isolated from the pneumatic valve channel layer by means of a PDMS film.

8. The microfluidic chip for the in-situ EIS detection of the *C. elegans* according to claim 1, wherein lateral electrodes in the EIS measurement electrodes of the micro-electrode array are liquid electrodes, wherein the lateral electrodes are in indirect contact with the EIS measurement chamber by means of slits of a fluidic channel rather than being in direct contact with the EIS measurement chamber.

* * * * *